United States Patent [19]
DeMarinis

[11] 3,957,984

[45] May 18, 1976

[54] SUBSTITUTED MERCAPTOACETAMIDOCEPHALOSPORINS

[75] Inventor: Robert M. DeMarinis, King of Prussia, Pa.

[73] Assignee: SmithKline Corporation, Philadelphia, Pa.

[22] Filed: Feb. 11, 1975

[21] Appl. No.: 548,949

Related U.S. Application Data

[62] Division of Ser. No. 389,407, Aug. 17, 1973, Pat. No. 3,883,520.

[52] U.S. Cl. ................................................ 424/246
[51] Int. Cl.² .......................................... A61K 31/54

[58] Field of Search .................................... 424/246

[56] References Cited
UNITED STATES PATENTS
3,641,021   2/1972   Ryan .............................. 260/243 C Primary Examiner—Jerome D. Goldberg
Attorney, Agent, or Firm—Stuart R. Suter; Alan D. Lourie; William H. Edgerton

[57] ABSTRACT

7-Cyanomethylmercaptoacetamidocephalosporins, 7-cyanomethylsulfinylacetamidocephalosporins, and 7-cyanomethylsulfonylacetamidocephalosporins, which have antibacterial activity, are disclosed.

24 Claims, No Drawings

SUBSTITUTED MERCAPTOACETAMIDOCEPHALOSPORINS

This is a division of application Ser. No. 389,407 filed Aug. 17, 1973, now U.S. Pat. No. 3,883,520.

This invention relates to cephalosporin compounds with cyanomethylmercaptoacetamido or the mono or dioxidized derivative at position 7 of the cephem nucleus. These compounds have antibacterial activity.

A wide variety of acyl groups have been used at position 7 of cephalosporin in the search for improved antibiotics. For example, 7-alkylmercaptoacetamidocephalosporanic acids have been disclosed in U.S. Pat. No. 3,297,692 and others. Also, 7-propargylmercaptoacetamidocephalosporins are disclosed in U.S. Pat. No. 3,278,531. However, cephalosporins with cyanomethylmercaptoacetamido or its oxidized derivatives in the 7-acyl moiety have not been described.

The compounds of this invention have the following structural formula

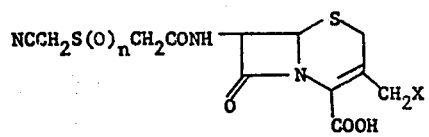

where
$n$ is 0, 1, or 2;
X is hydrogen, acetoxy, $OCH_3$, $SCH_3$, or SHet; and
Het is a 5 or 6 membered heterocyclic ring containing carbon and 1–4 atoms selected from the group consisting of N, O, and S, unsubstituted or substituted with one or two substituents selected from the group consisting of alkyl of $C_1$–$C_6$, alkoxy of $C_1$–$C_6$, allyloxy, oxide, halogen, carboxamido, carboxyl, carbalkoxy of $C_1$–$C_6$, mercapto, methylthio, trifluoromethyl, hydroxy, amino, alkylamino and dialkylamino, each undefined alkyl having 1–6 carbon atoms.

Het includes the N-oxide derivatives of the heterocyclic systems named where such derivatives are possible, for example, pyridyl-N-oxide.

A preferred group of compounds are those where X is SHet. Particularly preferred are compounds where Het is tetrazolyl, triazolyl, thiadiazolyl, oxadiazolyl, or pyridyl, unsubstituted or substituted. Preferred substituents are aklyl of $C_1$–$C_6$, hydroxy or mercapto.

Also within the scope of the invention are the nontoxic pharmaceutically acceptable salts of the acids defined by the formula given above. Many salts and methods of preparation are known within the art.

The compounds of the invention are prepared by acylation of a 7-aminocephalosporanic acid or a derivative thereof. The acylation agents are cyanomethylmercaptoacetic acid, cyanomethylsulfinylacetic acid, and cyanomethylsulfonylacetic acid or their activated derivatives. Common methods known to one skilled in the art such as mixed anhydride, acid halide, or activated ester may be used to activate the carboxyl group. Also a coupling reagent such as dicyclohexylcarbodiimide or N,N'-carbonyldiimidazole may be used to acylate esters of the cephalosporin nucleus.

The 7-aminocephalosporanic acids and derivatives are known in the art. Cyanomethylmercaptoacetic acid is prepared by reaction of chloroacetonitrile and mercaptoacetic acid in the presence of a base. Preparation of the other acylation agents or activated derivatives are done by standard methods or described herein.

The compounds of this invention have broadspectrum antibacterial activity with minimum inhibitory concentrations (MIC) ranging from 0.2 to >200 µg/ml when determined by standard agar inclusion methods. Table 1 shows MIC's for a variety of compounds within the scope of this invention against representative Gram-positive and Gram-negative bacteria.

The compounds of this invention are formulated and administered by injection in the same manner as other cephalosporins in dosages of from 250 to 1000 mg. The dosage is dependent on the age and weight of the subject and on the infection being treated and can be determined by those skilled in the art based on the data disclosed herein and experience with known cephalosporins.

TABLE 1

MIG (µg/ml)

| Compound Number | S. aureus HH 127 | S. aureus SK 23390 | S. aureus Villaluz | Strep. faecalis HH 34358 | E. coli SK 12140 | E. coli HH 33779 | Kleb. pneumo. SK 4200 | Kleb. pneumo. SK 1200 | Salmonella ATCC 12176 | Shigella parady-sentiae | Pseudo. aeruginosa HH63 | Serratia marc. ATCC 13880 | Entero. aerogenes ATCC 13048 |
|---|---|---|---|---|---|---|---|---|---|---|---|---|---|
| 79336 | 0.2 | 0.8 | 25 | 12.5 | 6.3 | 12.5 | 1.6 | 6.3 | 1.6 | 6.3 | >200 | >200 | >200 |
| 21436 | 0.2 | 0.1 | 25 | 6.3 | 1.6 | 6.3 | 1.6 | 0.8 | 1.6 | 1.6 | >200 | >200 | >200 |
| 94436 | 0.4 | 0.4 | 12.5 | 50 | 0.8 | 1.6 | 1.6 | 1.6 | 0.4 | 0.8 | >200 | >200 | 12.5 |
| 90246 | 1.6 | 1.6 | 25 | 50 | 6.3 | 25 | 25 | 6.3 | 3.1 | 6.3 | >200 | >200 | 50 |
| 09346 | 1.6 | 1.6 | 100 | 25 | 3.1 | 6.3 | 6.3 | 3.1 | 6.3 | 3.1 | >200 | >200 | 12.5 |
| 72346 | 1.6 | 1.6 | 25 | 50 | 1.6 | 3.1 | 1.6 | 1.6 | 1.6 | 1.6 | >200 | >200 | 6.3 |

* See Table 2 for structures

TABLE 2

| Compound No. | n | X |
|---|---|---|
| 79336 | 0 | acetoxy |
| 21436 | 0 | 5-methyl-1,3,4-thiadiazol-2-ylthio |
| 94436 | 0 | 1-methyltetrazol-5-ylthio |
| 90246 | 2 | acetoxy |
| 09346 | 2 | 5-methyl-1,3,4-thiadiazol-2-ylthio |
| 72346 | 2 | 1-methyltetrazol-5-ylthio |

The compounds are formulated in the same manner as other cephalosporins which are administered parenterally. The daily dose, which may be divided, may range from 1–5 g depending on the subject and the infection being treated.

The following examples illustrate the invention but are not to be construed as limiting the scope thereof.

PREPARATION 1

N-Hydroxysuccinimidyl cyanomethylmercaptoacetate

To a solution of cyanomethylmercaptoacetic acid (7.9 g, 60 mmol) and N-hydroxysuccinimide (6.9 g, 60 mmol) in tetraydrofuran (150 ml) was added in portions a solution of dicyclohexylcarbodiimide (12.4 g, 60 mmol) in tetrahydrofuran (35 ml). The reaction was stirred overnight at room temperature. The solid urea was filtered and washed with THF, the filtrate was concentrated to 25 ml, and additional urea was removed. The solution was evaporated and the product was recrystallized from chloroform; mp 90°–91°.

PREPARATION 2

N-Hydroxysuccinimidyl cyanomethylsulfinylacetate

While cooling in an ice bath, a solution of m-chloroperbenzoic acid (85%, 10 g, 50 mmol) in chloroform (200 ml) was added dropwise to a solution of N-hydroxysuccinimidyl cyanomethylmercaptoacetate (11.4 g, 50 mmol) in chloroform (150 ml). The reaction was allowed to warm to room temperature and was stirred overnight. The solvent was decanted and the gum was taken up in acetonitrile. Ether was added until a slight cloudiness developed and the solution was warmed gently until clarified. The product crystallized on cooling.

PREPARATION 3 cyanomethylsulfonylacetic acid

To a cooled, stirred solution of cyanomethylmercaptoacetic acid (26.2 g, 0.2 mol) in tetrahydrofuran (300 ml) was added dropwise a solution m-chloroperbenzoic acid (85%, 99 g, 0.5 mol) in tetrahydrofuran (400 ml.) The reaction was stirred at 0° for 10 minutes and then overnight at room temperature. The solvent was removed and the residue was washed with water (3 × 200 ml). The aqueous solution was allowed to stand 2 days, the precipitated solid was filtered, and the filtrate was lyophilized to give the product; mp 104°–105°.

EXAMPLE 1

7-Cyanomethylmercaptoacetamidocephalosporanic acid

Triethylamine was added to a suspension of 7-ACA (2.72 g, 10 mmol) in dimethylformamide (60 ml) until solution was effected. To this solution was added N-hydroxysuccinimidyl cyanomethylmercaptoacetate (2.28 g, 10 mmol) and the reaction was stirred at room temperature until tlc analysis indicated the reaction was completed (ca. 3 hours). The reaction was poured slowly with vigorous stirring into ether (1000 ml) and the precipitated solid was removed by filtration through filter aid. The filter cake was stirred with water (400 ml) containing triethylamine (4 ml) and then was filtered. The filtrate was acidified to pH 2.5 and extracted with ethyl acetate. The extracts were washed with water, dried, and concentrated to a small volume (ca. 20 ml) which contained the title product. A solution of sodium 2-ethylhexanoate was added followed by ether. The precipitated sodium salt of the product was collected, mp 178°–9°(dec).

EXAMPLE 2

7-Cyanomethylmercaptoacetamido-3-(5-methyl-1,3,4-thiadiazol-2-ylthiomethyl)-3-cephem-4-carboxylic acid 7-Amino-3-(5-methyl-1,3,4-thiadiazol-2-ylthiomethyl)-3-cephem-4-carboxylic acid (3.44 g, 10 mmol) was acylated with N-hydroxysuccinimidyl cyanomethylmercaptoacetate (2.28 g, 10 mmol) according to the procedure of Example 1 to give the title compound.

EXAMPLE 3

7-Cyanomethylmercaptoacetamido-3-(1-methyltetrazol-5-ylthiomethyl)-3-cephem-4-carboxylic acid The title compound was prepared by the reaction of 7-amino-3-(1-methyltetrazol-5-ylthiomethyl)-3-cephem-4-carboxylic acid (3.28 g, 10 mmol) and N-hydroxysuccininimidyl cyanomethylmercaptoacetate (3.4 g, 15 mmol) by the procedure of Example 1.

EXAMPLE 4

When an equimolar amount of the following 7-amino-3-heterocyclicthiomethyl-3-cephem-4-carboxylic acids are substituted for 7-aminocephalosporanic acid in the procedure of Example 1, the corresponding 7-cyanomethylmercaptoacetamido-3-heterocyclicthiomethyl-3-cephem-4-carboxylic acid is formed.

7-Amino-3-(tetrazol-5-ylthiomethyl)-3-cephem-4-carboxylic acid

7-Amino-3-(1,3,4-thiadiazol-2-ylthiomethyl)-3-cephem-4-carboxylic acid

7-Amino-3-(5-trifluoromethyl-1,3,4-thiadiazol-2-ylthiomethyl)-3-cephem-4-carboxylic acid 7-Amino-3-(5-ethyl-1,3,4-thiadiazol-2-ylthiomethyl)-3-cephem-4-carboxylic acid 7-Amino-3-(5-n-butyl-1,3,4-thiadiazol-2-ylthiomethyl)-3-cephem-4-carboxylic acid 7-Amino-3-(5-dimethylamino-1,3,4-thiadiazol-2-ylthiomethyl)-3-cephem-4-carboxylic acid 7-Amino-3-(5-mercapto-1,3,4-thiadiazol-2-ylthiomethyl)-3-cephem-4-carboxylic acid 7-Amino-3-(3-methylthio-1,2,4-thiadiazol-5-ylthiomethyl)-3-cephem-4-carboxylic acid 7-Amino-3-(3-methyl-1,2,4-thiadiazol-5-ylthiomethyl)-3-cephem-4-carboxylic acid 7-Amino-3-(1,2,4-triazol-3-ylthiomethyl)-3-cephem-4-carboxylic acid 7-Amino-3-(5-methyl-1,2,4-triazol-3-ylthiomethyl)-3-cephem-4-carboxylic acid 7-Amino-3-(4-methyl-1,2,4-triazol-3-ylthiomethyl)-3-cephem-4-carboxylic acid 7-Amino-3-(4,5-dimethyl-1,2,4-triazol-3-ylthiomethyl)-3-cephem-4-carboxylic acid 7-Amino-3-(2,5-dimethyl-1,2,4-triazol-3-ylthiomethyl)-3-cephem-4-carboxylic acid 7-Amino-3-(4-methyl-5-trifluoromethyl-1,2,4-triazol-3-ylthiomethyl)-3-cephem-4-carboxylic acid 7-Amino-3-(5-ethyl-1,2,4-triazol-3-ylthiomethyl)-3-cephem-4-carboxylic acid 7-Amino-3-(4-ethyl-1,2,4-triazol-3-ylthiomethyl)-3-cephem-4-carboxylic acid 7-Amino-3-(1methyl-1,2,4-triazol-5-ylthiomethyl)-3-cephem-4-carboxylic acid 7-Amino-3-(1-methyl-1,2,4-triazol-3-ylthiomethyl)-3-cephem-4-carboxylic acid 7-Amino-3-(1-ethyl-1,2,4-1,2,4-triazol-5-ylthiomethyl)-3-cephem-4-carboxylic acid 7-Amino-3-(1-ethyl-1,2,4-triazol-3-ylthiomethyl)-3-cephem-4-carboxylic acid 7-Amino-3-(4-allyl-1,2,4-triazol-3-ylthiomethyl)-3-cephem-4-carboxylic acid 7-Amino-3-(5-methoxymethyl-1,2,4-triazol-3-ylthiomethyl)-3-cephem-4-carboxylic acid 7-Amino-3-(5-cyclopropyl-1,2,4-triazol-3-ylthiomethyl)-3-cephem-4-carboxylic acid 7-Amino-3-(5-bromo-1,2,4-triazol-3-ylthiomethyl)-3-cephem-4-carboxylic acid 7-Amino-3-(5-hydroxy-4-methyl-1,2,4-triazol-3-ylthiomethyl)-3-cephem-4-carboxylic acid 7-Amino-3-(5-hydroxy-4-ethyl-1,2,4-triazol-3-ylthiomethyl)-3-cephem-4-carboxylic acid 7-Amino-3-(5-hydroxy-1,2,4-triazol-3-ylthiomethyl)-3-cephem-4-carboxylic acid 7-Amino-3-(1,2,3-triazol-4-ylthiomethyl)-3-cephem-4-carboxylic acid 7-Amino-3-(1-methyl-1,2,3-triazol-5-ylthiomethyl)3-cephem-4-carboxylic acid 7-Amino-3-(4-methyl-1,2,3-triazol-5-ylthiomethyl)-3-cephem-4-carboxylic acid 7-Amino-3-(1,3,4-oxadiazol-2-ylthiomethyl)-3-cephem-4-carboxylic acid 7-Amino-3-(5-methyl-1,3,4-oxadiazol-2-ylthiomethyl)-3-cephem-4-carboxylic acid 7-Amino-3-(4-pyrimidylthiomethyl)-3-cephem-4-carboxylic acid 7-Amino-3-(2-pyrazinylthiomethyl)-3-cephem-4-carboxylic acid 7-Amino-3-(3-pyridylthiomethyl)-3-cephem-4-carboxylic acid 7-Amino-3-(4-pyridylthiomethyl)-3-cephem-4-carboxylic acid 7-Amino-3-(1-oxide-2-pyridylthiomethyl)-3-cephem-4-carboxylic acid.

EXAMPLE 5

7-Cyanomethylsulfonylacetamidocephalosporanic acid

To a stirred solution of t-butyl 7-aminocephalosporanate (3.3 g, 10 mmol) and coanomethylsulfonylacetic acid (1.6 g, 10 mmol) in tetrahydrofuran (30 ml) was added dropwise a solution of dicyclohexylcarbodiimide (2.1 g, 10 mmol) in tetrahydrofuran (20 ml). The reaction was stirred at room temperature for 4 hours and filtered. The filtrate was evaporated and the residue was chromatographed on silica gel (75 g) with 1:1 ethyl acetate: benzene as eluent. The purified ester (1.57 g, 3.3 mmol) in acetonitrile (15 ml) was warmed to effect complete solution and then trifluoroacetic acid (15 ml) was added. The reaction was allowed to stand for 4 hours and the precipitated title product was collected, triturated with acetonitrile and ether and dried.

EXAMPLE 6

7-Cyanomethylsulfonylacetamido-3-(5-methyl-1,3,4,-thiadiazol-2-ylthiomethyl)-3-cephem-4-carboxylic acid t-Butyl 7-amino-3-(5-methyl-1,3,4-thiadiazol-2-ylthiomethyl)-3-cephem-4-carboxylate (8.0 g, 20 mmol), cyanomethylsulfonylacetic acid (3.3 g, 20 mmol) and dicyclohexylcarbodiimide (4.1 lg, 20 mmol) were reacted by the procedure of Example 5. The crude ester was chromatographed on silica gel using ethyl acetate as eluent. The purified t-butyl ester (6.2 g) was dissolved in hot acetonitrile (40 ml) and trifluoroacetic acid (40 ml) was added. The solution was allowed to stand 2.5 hours and then was added slowly to ether (100 ml) with stirring. The precipitated title compound was collected, triturated with ether and dried.

EXAMPLE 7

7-Cyanomethylsulfonylacetamido-3-(1-methyltetrazol-5-ylthiomethyl)-3-cephem-4-carboxylic acid t-Butyl 7-amino-3-(1-methyltetrazol-5-ylthiomethyl)-0-cephem-4-carboxylate (5.75 g, 15 mmol), cyanomethylsulfonylacetic acid (2.45 g, 15 mmol), and dicyclohexylcarbodiimide (3.1 g, 15 mmol) were reacted as in Example 6. The t-butyl ester was treated with trifluoroacetic acid for 20 minutes as in Example 6, to give the title compound.

EXAMPLE 8

When an equimolar amount of the t-butyl esters of the following 7-amino-3-heterocyclicthiomethyl-3-cephem-4-carboxylic acids are substituted for t-butyl 7-amino-3-(5-methyl-1,3,4-thiadiazol-2--ylthiomethyl)-3-cephem-4-carboxylate in the procedure of Example 6, the corresponding 7-cyanomethylsulfonylacetamido-3-heterocyclicthiomethyl-3-cephem-4-carboxylic acid is formed.

7-Amino-3-(tetrazol-5-ylthiomethyl)3-cephem-4-carboxylic acid

7-Amino-3-(1,3,4-thiadiazol-2-ylthiomethyl)-3-cephem-4-carboxylic acid

7-Amino-3-(5-trifluoromethyl-1,3,4-thiadiazol-2-ylthiomethyl)-3-cephem-4-carboxylic acid 7-Amino-3-(5-ethyl-1,3,4-thiadiazol-2-ylthiomethyl)-3-cephem-4-carboxylic acid 7-Amino-3-(5-n-butyl-1,3,4-thiadiazol-2-ylthiomethyl)-3-cephem-4-carboxylic acid 7-Amino-3-(5-dimethylamino-1,3,4-thiadiazol-2-ylthiomethyl)-3-cephem-4-carboxylic acid -

7-Amino-3-(tetrazol-5-ylthiomethyl)-3-cephem-4-carboxylic acid

7-Amino-3-(3-methylthio-1,2,4-thiadiazol-5-ylthiomethyl)-3-cephem-4-carboxylic acid 7-Amino-3-(3-methyl-1,2,4-thiadiazol-5-ylthiomethyl)-3-cephem-4-carboxylic acid 7-Amino-3-(1,2,4-triazol-3-ylthiomethyl)-3-cephem-4-carboxylic acid 7-Amino-3-(5-methyl-1,2,4-triazol-3-ylthiomethyl)-3-cephem-4-carboxylic acid 7-Amino-3-(4-methyl-1,2,4-triazol-3-ylthiomethyl)-3-cephem-4-carboxylic acid 7-Amino-3-(4,5-dimethyl-1,2,4-triazol-3-ylthiomethyl)-3-cephem-4-carboxylic acid 7-Amino-3-(2,5-dimethyl-1,2,4-triazol-3-ylthiomethyl)-3-cephem-4-carboxylic acid 7-Amino-3-(4-methyl-5-trifluoromethyl-1,2,4-triazol-3-ylthiomethyl)-3-cephem-4-carboxylic acid 7-Amino-3-(5-ethyl-1,2,4-triazol-3-ylthiomethyl)-3-cephem-4-carboxylic acid 7-Amino-3-(4-ethyl-1,2,4-triazol-3-ylthiomethyl)-3-cephem-4-carboxylic acid 7-Amino-3-(1-methyl-1,2,4-triazol-5-ylthiomethyl)-3-cephem-4-carboxylic acid 7-Amino-3-(1-methyl-1,2,4-triazol-3-ylthiomethyl)-3-cephem-4-carboxylic acid 7-Amino-3-(1-ethyl-1,2,4-triazol-5-ylthiomethyl)-3-cephem-4-carboxylic acid 7-Amino-3-(1-ethyl-1,2,4-triazol-3-ylthiomethyl)-3-cephem-4-carboxylic acid 7-Amino-3-(4-allyl-1,2,4-triazol-3-ylthiomethyl)-3-cephem-4-carboxylic acid 7-Amino-3-(5-methoxymethyl-1,2,4-triazol-3-ylthiomethyl)-3-cephem-4-carboxylic acid 7-Amino-3-(5-cyclopropyl-1,2,4-triazol-3-ylthiomethyl)-3-cephem-4-carboxylic acid 7-Amino-3-(5-bromo-1,2,4-triazol-3-ylthiomethyl)-3-cephem-4-carboxylic acid 7-Amino-3-(5-hydroxy-4-methyl-1,2,4-triazol-3-ylthiomethyl)-3-cephem-4-carboxylic acid 7-Amino-3-(5-hydroxy-4-ethyl-1,2,4-triazol-3-ylthiomethyl)-3-cephem-4-carboxylic acid 7-Amino-3-(5-hydroxy-1,2,4-triazol-3-ylthiomethyl)-3-cephem-4-carboxylic acid 7-Amino-3-(1-methyl-1,2,3-triazol-5-ylthiomethyl)-3-cephem-4-carboxylic acid 7-Amino-3-(1,3,4-oxadiazol-2-ylthiomethyl)-3-cephem-4-carboxylic acid 7-Amino-3-(5-methyl-1,3,4-oxadiazol-2-ylthiomethyl)-3-cephem-4-carboxylic acid 7-Amino-3-(4-pyrimidylthiomethyl)-3-cephem-4-carboxylic acid 7-Amino-3-(2-pyrazinylthiomethyl)-3-cephem-4-carboxylic acid 7-Amino-3-(3-pyridylthiomethyl)-3-cephem-4-carboxylic acid 7-Amino-3-(4-pyridylthiomethyl)-3-cephem-4-carboxylic acid 7-Amino-3-(1-oxide-2-pyridylthiomethyl)-3-cephem-4-carboxylic acid.

EXAMPLE 9

When 7-aminocephalosporanic acid, 7-amino-3-(5-methyl-1,3,4-thiadiazol-5-ylthiomethyl)-3-cephem-4-carboxylic acid, and 7-amino-3-(1-methyltetrazol-5-ylthiomethyl)-3-cephem-4-carboxylic acid are acylated with N-hydroxysuccinimidyl cyanomethylsulfinylacetate according to the procedure used in Example 1 the following compounds are obtained:

7-cyanomethylsulfinylacetamidocephalosporanic acid 7-cyanomethylsulfinylacetamido-3-(5-methyl-1,3,4-thiadiazol-2-ylthiomethyl)-3-cephem-4-carboxylic acid 7-cyanomethylsulfinylacetamido-3-(1-methyltetrazol-5-ylthiomethyl)-3-cephem-4-carboxylic acid.

EXAMPLE 10

When an equimolar amount of the 7-amino-3-heterocyclicthiomethyl-3-cephem-4-carboxylic acids enumerated in Example 4 are substituted for 7-amino-3-(5-methyl-1,3,4-thiadiazol-2-ylthiomethyl)-3-cephem-4-carboxylic acid in the procedure of Example 9, the corresponding 7-cyanomethylsulfinylacetamido-3-heterocyclicthiomethyl-3-cephem-4-carboxylic acid is formed.

EXAMPLE 11

Cyanomethylsulfonylacetic acid is reacted with N-hydroxysuccinimide according to the procedure of Preparation 1 to give the activated ester which is reacted at once with 7-amino-3-(1,2,3-triazol-4-ylthiomethyl)-3-cephem-4-carboxylic acid to give 7-cyanomethylsulfonylacetamido-3-(1,2,3-triazol-4-ylthiomethyl)-3-cephem-4-carboxylic acid. 7-Cyanomethylsulfonylacetamido-3-(4-methyl-1,2,3-triazol-5-ylthiomethyl)-3-cephem-4-carboxylic acid is prepared in a similar manner.

EXAMPLE 12

When 7-aminodesacetoxycephalosporanic acid (7-ADCA) is acylated according to the procedure of Example 1 with N-hydroxysuccinimidyl cyanomethylmercaptoacetate and N-hydroxysuccinimidyl cyanomethylsulfinylacetate, 7-cyanomethylmercaptoacetamido-3-methyl-3-cephem-4-carboxylic acid and 7-cyanomethylsulfinylacetamido-3-methyl-3-cephem-4-carboxylic acid are obtained.

When the t-butyl ester of 7-ADCA is acylated with cyanomethylsulfonylacetic acid by the procedure of Example 5, 7-cyanomethylsulfonylacetamido-3-methyl-3-cephem-4-carboxylic acid is obtained.

EXAMPLE 13

Using the procedure of Example 1, 7-amino-3-methoxymethyl-3-cephem-4-carboxylic acid is acylated with N-hydroxysuccinimidyl cyanomethylmercaptoacetate and N-hydroxysuccinimidyl cyanomethylsulfinylacetate to give 7-cyanomethylmercaptoacetamido-3-methoxymethyl-3-cephem-4-carboxylic acid and 7-cyanomethylsulfinylacetamido-3-methoxymethyl-3-cephem-4-carboxylic acid.

7-Cyanomethylsulfonylacetamido-3-methoxymethyl-3-cephem-4-carboxylic acid is obtained when t-butyl 7-amino-3-methoxymethyl-3-cephem-4-carboxylate is substituted for t-butyl 7-aminocephalosporanate in Example 5.

EXAMPLE 14

Substitution of 7-amino-3-methylmercaptomethyl-3-cephem-4-carboxylic acid or its t-butyl ester for 7-amino-3-methoxymethyl-3-cephem-4-carboxylic acid or its t-butyl ester in Example 12 gives the following products:

7-cyanomethylmercaptoacetamido-3-methylmercaptomethyl-3-cephem-4-carboxylic acid 7-cyanomethylsulfinylacetamido-3-methylmercaptomethyl-3-cephem-4-carboxylic acid 7-cyanomethylsulfonylacetamido-3-methylmercaptomethyl-3-cephem-4-carboxylic acid

EXAMPLE 15

An injectable pharmaceutical composition is prepared by dissolving 100–500 mg of sodium 7-cyanomethylsulfonylacetamido-3-(1-methyltetrazol-5-ylthiomethyl)-3-cephem-4-carboxylate in sterile water or sterile normal saline solution (1–2 ml). All other cephalosporins within the formula I including each compound enumerated in the above examples are formulated in a similar manner.

I claim:

1. A pharmaceutical composition comprising an antibacterially effective amount of a compound of the formula

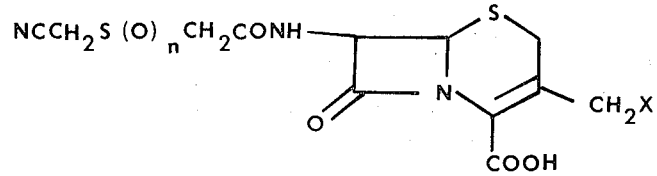

where
n is 0, 1, or 2;
X is SHet; and
Het is a 5 or 6-membered heterocyclic ring containing carbon and 1–4 atoms selected from the group consisting of N, O, and S, unsubstituted or substituted with one or two substituents selected from the group consisting of alkyl of $C_1$–$C_6$, alkoxy of $C_1$–$C_6$, allyloxy, oxide, halogen, carboxamido, carboxyl, carbalkoxy of $C_1$–$C_6$, mercapto, methylthio, trifluoromethyl, hydroxy, amino, alkylamino and dialkylamino, each undefined alkyl having 1–6 carbon atoms or a non-toxic pharmaceutically acceptable salt thereof and a pharmaceutically acceptable carrier therefor.

2. A pharmaceutical composition comprising an antibacterially effective amount of a compound as claimed in claim 1 where n is 0 amd a pharmaceutically acceptable carrier therefor.

3. A pharmaceutical composition comprising an antibacterially effective amount of a compound as claimed in claim 1 where n is 1 and a pharmaceutically acceptable carrier therefor.

4. A pharmaceutical composition comprising an antibacterially effective amount of a compound as claimed in claim 1 where n is 2 and a pharmaceutically acceptable carrier therefor.

5. A pharmaceutical composition comprising an antibacterially effective amount of a compound as claimed in claim 2 where X is SHet and Het is tetrazolyl thiadiazolyl, triazolyl, oxadiazolyl, or pyridyl, unsubstituted or substituted with one or two substituents selected from the group consisting of alkyl of $C_1$–$C_6$, hydroxy, and mercapto and a pharmaceutically acceptable carrier therefor.

6. A pharmaceutical composition comprising an antibacterially effective amount of a compound as claimed in claim 3 where X is SHet and Het is tetrazolyl, thiadiazolyl, triazolyl, oxadiazolyl, or pyridyl, unsubstituted or substituted with one or two substituents selected from the group consisting of alkyl of $C_1$–$C_6$, hydroxy, and mercapto and a pharmaceutically acceptable carrier therefor.

7. A pharmaceutical composition comprising an antibacterially effective amount of a compound as claimed in claim 4, where X is SHet and Het is tetrazolyl, thiadiazolyl, triazolyl, oxadiazolyl, or pyridyl, unsubstituted or substituted with one or two substituents selected from the group consisting of alkyl of $C_1$–$C_6$, hydroxy, and mercapto and a pharmaceutically acceptable carrier therefor.

8. A pharmaceutical composition comprising an antibacterially effective amount of a compound as claimed in claim 2 being the compound 7-cyanomethylmercaptoacetamido-3-(5-methyl-1,3,4-thiadiazol-2-ylthiomethyl)-3-cephem-4-carboxylic acid and a pharmaceutically acceptable carrier therefor.

9. A pharmaceutical composition comprising an antibacterially effective amount of a compound as claimed in claim 2 being the compound 7-cyanomethylmercaptoacetamido-3-(1-methyltetrazol-5-ylthiomethyl)-3-cephem-4-carboxylic acid and a pharmaceutically acceptable carrier therefor.

10. A pharmaceutical composition comprising an antibacterially effective amount of a compound as claimed in claim 3 being the compound 7-cyanomethylsulfinylacetamido-3-(1-methyltetrazol-5-ylthiomethyl)-3-cephem-4-carboxylic acid and a pharmaceutically acceptable carrier therefor.

11. A pharmaceutical composition comprising an antibacterially effective amount of a compound as claimed in claim 4 being the compound 7-cyanomethylsulfonylacetamido-3-(5-methyl-1,3,4-thiadiazol-2-ylthiomethyl)-3-cephem-4-carboxylic acid and a pharmaceutically acceptable carrier therefor;

12. A pharmaceutical composition comprising an antibacterially effective amount of a compound as claimed in claim 4 being the compound 7-cyanomethylsulfonylacetamido-3-(1-methyltetrazol-5-ylthiomethyl)-3-cephem-4-carboxylic acid and a pharmaceutically acceptable carrier therefor.

13. A method of treating bacterial infections comprising administering by injection to a warm-blooded animal an effective but non-toxic dose of 250–1000 mg of a compound of the formula

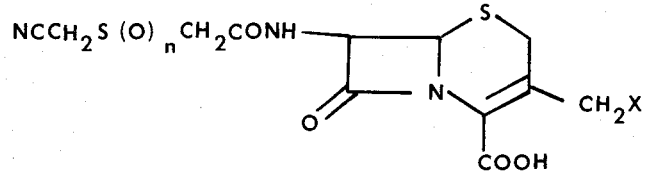

wherein
n is 0, 1, or 2;
X is SHet; and
Het is a 5 or 6-membered heterocyclic ring containing carbon and 1–4 atoms selected from the group consisting of N, O, and S, unsubstituted or substituted with one or two substituents selected from the group consisting of of N, O, and S, unsubstituted or substituted with one or two substituents selected from the group consisting of alkyl of $C_1$–$C_6$, alkoxy of $C_1$–$C_6$, allyloxy, oxide, halogen, carboxamido, carboxyl, carbalkoxy of $C_1$–$C_6$, mercapto, methylthio, trifluoromethyl, hydroxy, amino, alkylamino and dialkylamino, each undefined alkyl having 1–6 carbon atoms or a non-toxic pharmaceutically acceptable salt thereof.

14. A method of treating bacterial infections comprising administering by injection to a warm-blooded animal an effective but non-toxic dose of 250–1000 mg of a compound as claimed in claim 13 wherein n is 0.

15. A method of treating bacterial infections comprising administering by injection to a warm-blooded animal an effective but non-toxic dose of 250–1000 mg of a compound as claimed in claim 13 where n is 1.

16. A method of treating bacterial infections comprising administering by injection to a warm-blooded animal an effective but non-toxic dose of 250–1000 mg of a compound as claimed in claim 13 where n is 2.

17. A method of treating bacterial infections comprising administering by injection to a warm-blooded animal an effective but non-toxic dose of 250–1000 mg of a compound as claimed in claim 14 where X is SHet and Het is tetrazolyl, thiadiazolyl, triazolyl, oxadiazolyl, or pyridyl, unsubstituted or substituted with one or two substituents selected from the group consisting of alkyl of $C_1$–$C_6$, hydroxy, and mercapto.

18. A method of treating bacterial infections comprising administering by injection to a warm-blooded animal an effective but non-toxic dose of 250–1000 mg of a compound as claimed in claim 15 where X is SHet and Het is tetrazolyl, thiadiazolyl, triazolyl, oxadiazolyl, or pyridyl, unsubstituted or substituted with one or two substituents selected from the group consisting of alkyl of $C_1$–$C_6$, hydroxy, and mercapto.

19. A method of treating bacterial infections comprising administering by injection to a warm-blooded animal an effective but non-toxic dose of 250–1000 mg of a compound as claimed in claim 16 where X is SHet and Het is tetrazolyl, thiadiazolyl, triazolyl, oxadiazolyl, or pyridyl, unsubstituted or substituted with one or two substituents selected from the group consisting of alkyl of $C_1$–$C_6$, hydroxy, and mercapto.

20. A method of treating bacterial infections comprising adminstering by injection to a warm-blooded animal an effective but non-toxic dose of 250–1000 mg of a compound as claimed in claim 17 being the compound 7-cyanomethylmercaptoacetamido-3-(5-methyl-1,3,4-thiadiazol-2-ylthiomethyl)-3-cephem-4-carboxylic acid.

21. A method of treating bacterial infections comprising administering by injection to a warm-blooded animal an effective but non-toxic dose of 250–1000 mg of a compound as claimed in claim 17 being the compound 7-cyanomethylmercaptoacetamido-3-(1-methyltetrazol-5-ylthiomethyl)-3-cephem-4-carboxylic acid.

22. A method of treating bacterial infections comprising administering by injection to a warm-blooded animal an effective but non-toxic dose of 250–1000 mg of a compound as claimed in claim 18 being the compound 7-cyanomethylsulfinylacetamido-3-(1-methyltetrazol-5-ylthiomethyl)-3-cephem-4-carboxylic acid.

23. A method of treating bacterial infections comprising administering by injection to a warm-blooded animal an effective but non-toxic dose of 250–1000 mg of a compound as claimed in claim 19, being the compound 7-cyanomethylsulfonylacetamido-3-(5-methyl-1,3,4-thiadiazol-2-ylthiomethyl)-3-cephem-4-carboxylic acid.

24. A method of treating bacterial infections comprising administering by injection to a warm-blooded animal an effective but non-toxic dose of 250–1000 mg of a compound as claimed in claim 19 being the compound 7-cyanomethylsulfonylacetamido-3-(1-methyltetrazol-5-ylthiomethyl)-3-cephem-4-carboxylic acid.

* * * * *

UNITED STATES PATENT OFFICE
CERTIFICATE OF CORRECTION

Patent No. 3,957,984      Dated May 18, 1976

Inventor(s) Robert M. DeMarinis

It is certified that error appears in the above-identified patent and that said Letters Patent are hereby corrected as shown below:

Column 3, line 7:    "tetraydrofuran" should read -- tetrahydrofuran --

Column 4, line 67:    "1,2,4-1,2,4" should read -- 1,2,4 --

Column 5, line 42:    "coanomethylsulfonylacetic" should read -- cyanomethylsulfonylacetic --

Column 5, line 62:    "4.1 Ig" should read -- 4.1g --

Column 6, line 9:    "O-cephem" should read -- 3-cephem --

Column 6, line 37:    "7-Amino-3-(tetrazol-5-ylthiomethyl" should read -- 7-Amino-3-(5-mercapto-1,3,4-thiadiazol-2-ylthiomethyl) --

Signed and Sealed this

Twenty-eighth Day of December 1976

[SEAL]

Attest:

RUTH C. MASON  
*Attesting Officer*

C. MARSHALL DANN  
*Commissioner of Patents and Trademarks*